(12) United States Patent
Taguchi et al.

(10) Patent No.: US 6,407,228 B1
(45) Date of Patent: Jun. 18, 2002

(54) METHOD FOR THE PREPARATION OF β-LACTAM COMPOUND

(75) Inventors: Yoichi Taguchi; Akihiro Oishi; Isao Shibuya; Tohru Tsuchiya, all of Tsukuba (JP)

(73) Assignee: Japan as represented by Director General of Agency of Industrial Science and Technology, Tokyo-to (JP)

( * ) Notice: Subject to any disclaimer, the term of this patent is extended or adjusted under 35 U.S.C. 154(b) by 1204 days.

(21) Appl. No.: 08/527,217

(22) Filed: Sep. 12, 1995

(30) Foreign Application Priority Data

Sep. 30, 1994 (JP) ............................................... 6-237301

(51) Int. Cl.$^7$ ............................................ C07D 205/08
(52) U.S. Cl. ...................................................... 540/360
(58) Field of Search ......................................... 540/360

(56) References Cited

PUBLICATIONS

Arnoldi, Eur. J. Med. Chem 23, 149 (1988).*
Hirai, Chem. Pharm. Bull. 21 1090 (1973).*

* cited by examiner

*Primary Examiner*—Mark L Berch
(74) *Attorney, Agent, or Firm*—Wenderoth, Lind & Ponack, LLP

(57) ABSTRACT

A simple and efficient method is proposed for the preparation of a β-lactam compound such as 1-phenyl-4-ethoxy-2-azetidinone which can be produced by mixing an isocyanate compound such as phenyl isocyanate and a vinyl ether compound such as ethyl vinyl ether and heating the mixture at a moderate temperature under a superatmospheric pressure of up to 12000 atmospheres.

3 Claims, No Drawings

METHOD FOR THE PREPARATION OF β-LACTAM COMPOUND

BACKGROUND OF THE INVENTION

The present invention relates to a novel method for the preparation of a β-lactam compound. More particularly, the present invention relates to an efficient method for the preparation of a β-lactam compound having usefulness as an intermediate of β-aminoacid derivatives and certain antibiotics having a chemical structure resembling that of penicillin.

As is known, β-lactam ring forms the principal skeletal structure of a large number of antibiotics including penicillin as a typical example to play a core role in the physiological activity thereof. Accordingly, various synthetic methods have been reported for the preparation of a great number of β-lactam compounds while most of these prior art methods have a disadvantage that synthetic procedure involves complicated steps due to the high reactivity of the β-lactam ring so that it is eagerly desired to develop a simple and efficient method for the synthetic preparation of β-lactam compounds.

On the other hand, it is also known that various β-amino acids can be obtained from β-lactam compounds by the reaction thereof with alcohols and other reagents by virtue of the high chemical reactivity of the β-lactam ring.

Known methods for the synthetic preparation of a β-lactam compound include a method in which an isocyanate compound and an alkene compound are reacted. See, for example, "Comprehensive Heterocyclic Chemistry", ed. by A. R. Katritzlky, et al., Pergamon Press, Oxford (1984), pages 237–362 and "High Pressure Chemical Synthesis", ed. by J. Jurczak, et al., Elsevier (1989), pages 255–293. Although this method is advantageous because the reaction proceeds in one step to form the β-lactam ring, the method has a disadvantage relative to the applicability thereof when a variety of β-lactam compounds are desired because the reactivity between the reactants can be high enough only when the isocyanate compound as one of the reactants has a strongly electron-attractive group as in chlorosulfonyl isocyanate and the like or when an isocyanate compound is combined with a specific alkene compound such as allene, 2,3-dihydrofuran and the like.

With an object to provide a simple and efficient method for the synthetic preparation of a β-lactam compound capable of overcoming the above described disadvantages in the prior art methods, the inventors have continued extensive investigations and previously discovered that a specific β-lactam compound can be prepared by the reaction of 2,3-dihydrofuran and an isocyanate compound under specific conditions but the versatility of the method is still not good enough.

SUMMARY OF THE INVENTION

The present invention accordingly has an object to provide a novel method with high efficiency and versatility for the synthetic preparation of various kinds of β-lactam compounds to be freed from the above described disadvantages and limitations in the prior art methods.

Thus, the method of the present invention for the preparation of a β-lactam compound represented by the general formula

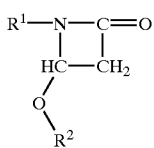

(I)

in which $R^1$ and $R^2$ are, each independently from the other, a monovalent hydrocarbon group, comprises the steps of: (a) mixing an isocyanate compound represented by the general formula $$R^1NCO, \qquad (II)$$

in which $R^1$ has the same meaning as defined above, and a vinyl ether compound represented by the general formula $$CH_2=CH-O-R^2, \qquad (III)$$

in which $R^2$ has the same meaning as defined above, to form a reaction mixture; and (b) bringing the reaction mixture under a superatmospheric pressure of at least 2000 atmospheres.

Although the reaction between the isocyanate compound and the vinyl ether compound under a high pressure can proceed even at room temperature, it is preferable that the reaction mixture is heated at an elevated temperature of up to 200° C. or, preferably, up to 130° C. when acceleration of the reaction is desired.

DETAILED DESCRIPTION OF THE PREFERRED EMBODIMENTS

As is described above, the procedure of the inventive method for the preparation of a β-lactam compound is very simple and efficient because the synthetic reaction can proceed only by bringing a reaction mixture of the starting reactants under a superatmospheric pressure to give the desired compound in a high yield.

One of the starting reactants is an isocyanate compound represented by the above given general formula (II). In this general formula, $R^1$ is a monovalent hydrocarbon group exemplified by straight-chain or branched alkyl groups having 1 to 20 carbon atoms such as methyl, ethyl, n-propyl, isopropyl, n-butyl, isobutyl, sec-butyl, tert-butyl, pentyl, hexyl, heptyl, octyl, nonyl, decyl, dodecyl, tetradecyl, pentadecyl, hexadecyl, octadecyl and eicosyl groups, cycloalkyl groups having 3 to 20 carbon atoms such as cyclopropyl, cyclobutyl, cyclopentyl, cyclohexyl, cyclooctyl, methyl cyclohexyl and decahydronaphthyl groups, aryl groups having 6 to 20 carbon atoms such as phenyl, tolyl, xylyl, naphthyl and anthracyl groups as well as substituted aryl groups having substituent groups including halogen atoms, e.g., chlorine, bromine and fluorine atoms, alkyl groups, e.g., methyl, ethyl, propyl and butyl groups, and alkoxy groups, e.g., methoxy, ethoxy, propoxy and butoxy groups, such as chlorophenyl, bromophenyl, fluorophenyl and ethylphenyl groups, and aralkyl groups having 7 to 20 carbon atoms such as benzyl and 2-phenylethyl groups as well as substituted aralkyl groups having substituents which can be the same ones as in the above mentioned substituted aryl groups, such as methyl benzyl group.

Particular examples of the isocyanate compound represented by the general formula (II) and suitable as the starting reactant in the inventive method include: alkyl isocyanates such as methyl isocyanate, ethyl isocyanate, propyl isocyanate, butyl isocyanate, pentyl isocyanate and hexyl isocyanate; cycloalkyl isocyanates such as cyclopentyl isocyanate and cyclohexyl isocyanate; and unsubstituted and substituted aryl isocyanates such as phenyl isocyanate, naphthyl isocyanate, chlorophenyl isocyanate, bromophenyl isocyanate, fluorophenyl isocyanate, tolyl isocyanate, xylyl isocyanate and ethylphenyl isocyanate; and aralkyl isocyanates such as benzyl isocyanate and phenylethyl isocyanate.

The other of the starting reactants to be reacted with the above described isocyanate compound is a vinyl ether compound represented by the general formula (III), in which $R^2$ is a monovalent hydrocarbon group including: straight-chain or branched alkyl groups having 1 to 20 carbon atoms such as methyl, ethyl, n-propyl, isopropyl, n-butyl, isobutyl, sec-butyl, tert-butyl, pentyl, hexyl, heptyl, octyl, nonyl, decyl, dodecyl, tetradecyl, pentadecyl, hexadecyl, octadecyl and eicosyl groups; and cycloalkyl groups having 3 to 20 carbon atoms such as cyclopropyl, cyclobutyl, cyclopentyl, cyclohexyl, cyclooctyl, methyl cyclohexyl and decahydronaphthyl groups.

Particular examples of the vinyl ether compound represented by the general formula (III) and suitable as the starting reactant in the reaction of the inventive method include: alkyl vinyl ethers such as methyl vinyl ether, ethyl vinyl ether, propyl vinyl ether, butyl vinyl ether, pentyl vinyl ether, hexyl vinyl ether, 2-ethylhexyl vinyl ether and decyl vinyl ether; and cycloalkyl vinyl ethers such as cyclopentyl vinyl ether and cyclohexyl vinyl ether.

The reaction of the isocyanate compound of the general formula (II) and the vinyl ether compound of the general formula (III) proceeds in a molar ratio of 1:1 of these reactants but it is usually preferable that the vinyl ether compound is used in a large excess over the isocyanate compound so that the excess amount of the vinyl ether compound serves as a diluent of the reaction mixture although it is optional that the vinyl ether compound is used in an amount of 0.8 to 1.2 moles per mole of the isocyanate compound and the reaction mixture is diluted with a conventional inert organic solvent, which should preferably have relatively low polarity, such as hydrocarbon solvents, e.g., benzene, toluene, xylene and the like.

The reaction between the isocyanate compound and the vinyl ether compound proceeds by bringing the reaction mixture under a superatmospheric pressure which should preferably be as high as possible. The pressure should desirably be at least 2000 atmospheres or, preferably, in the range from 2000 to 12000 atmospheres. The reaction temperature is not particularly limitative and the reaction can proceed even at room temperature although the reaction can be accelerated by increasing the temperature while an excessively high temperature is disadvantageous due to increase in the side reactions. In consideration of the balance between the reaction velocity and side reactions, the reaction temperature should be in the range from 20 to 130° C. The reaction time naturally depends on various factors such as the kinds of the reactants, pressure, reaction temperature and the like but the reaction is usually complete within 1 to 50 hours. In this way, the desired β-lactam compound can be obtained in a high yield of, for example, 90% or even higher of the theoretical value though dependent on various conditions.

In the following, the method of the present invention is described in more detail by way of examples.

EXAMPLE 1

A Teflon tube containing a mixture of 0.84 g (7.1 mmoles) of phenyl isocyanate and 1.75 g (24 mmoles) of ethyl vinyl ether was sealed and introduced into a high-pressure reactor and the mixture was heated at 100° C. under a pressure of 8000 atmospheres for 20 hours. The reaction mixture taken out was evaporated and then subjected to distillation under reduced pressure to obtain a reaction product which could be identified from the results of the instrumental analyses shown below to be the desired 1-phenyl-4-ethoxy-2-azetidinone which was the β-lactam compound of the general formula (I) with $R^1$ and R2 being a phenyl group and ethyl group, respectively. The yield of the product was 93% of the theoretical value. The thus obtained β-lactam compound was found to have strong antibacterial activity.

The analysis for the identification of the reaction product was performed by the infrared absorption spectrophotometry (IR), mass spectrometry (MS) and nuclear magnetic resonance absorption spectroscopy ($^1$H-NMR and $^{13}$C-NMR) to give the results shown below.

IR: 1763 cm$^{-1}$ (lactam C=O);
MS (m/z): 191 (M$^+$) (corresponding to $C_{11}H_{13}O_2N$);
$^1$H-NMR: 1.07 (t, 3H); 2.69–2.98 (m, 2H); 3.30–3.5 (m, 2H); 5.22 (t, 1H); 6.94 (t, 1H); 7.17 (t, 2H); 7.36 (d, 2H);
$^{13}$C-NMR: 163.16; 137.61; 129.05; 124.08; 116.69; 80.05; 61.02; 43.59; 15.06.

For comparison, the same reaction mixture as above in a sealed Teflon tube was heated at 100° C. for 20 hours without pressurization to find that the yield of 1-phenyl-4-ethoxy-2-azetidinone was only 2% of the theoretical value according to the result of the GLC analysis of the reaction mixture.

EXAMPLE 2

A Teflon tube containing a mixture of 0.37 g (3.1 mmoles) of phenyl isocyanate and 0.94 g (6.0 mmoles) of 2-ethylhexyl vinyl ether was sealed and introduced into a high-pressure reactor and the mixture was heated at 100° C. under a pressure of 8000 atmospheres for 20 hours. The reaction mixture taken out was purified by the method of dry-column chromatography in a silica gel column with a 2:1 mixture of hexane and ethyl acetate as the eluant to obtain a reaction product which could be identified from the results of the IR and MS analyses shown below to be the desired 1-phenyl-4-(2-ethylhexyl)oxy-2-azetidinone which was the β-lactam compound of the general formula (I) with $R^1$ and $R^2$ being a phenyl group and 2-ethyl-hexyl group, respectively. The yield of the product was 87% of the theoretical value.

IR: 1767 cm$^{-1}$ (lactam C=O);
MS (m/z): 275 (M$^+$) (corresponding to $C_{17}H_{25}O_2N$).

EXAMPLE 3

A Teflon tube containing a mixture of 0.20 g (3.5 mmoles) of methyl isocyanate and 0.41 g (5.7 mmoles) of ethyl vinyl ether was sealed and introduced into a high-pressure reactor and the mixture was heated at 100° C. under a pressure of 8000 atmospheres for 20 hours. The reaction mixture taken out was evaporated and then purified by distillation under reduced pressure to obtain a reaction product which could be identified from the results of the IR and MS analyses shown below to be the desired 1-methyl-4-ethoxy-2-azetidinone which was the β-lactam compound of the general formula (I) with $R^1$ and $R^2$ being a methyl group and ethyl group, respectively. The yield of the product was 21% of the theoretical value.

IR: 1755 cm$^{-1}$ (lactam C=O);
MS (m/z): 129 (M$^+$) (corresponding to $C_6H_{11}O_2N$).

EXAMPLE 4

A Teflon tube containing a mixture of 0.17 g (3.0 mmoles) of methyl isocyanate and 0.57 g (5.7 mmoles) of butyl vinyl ether was sealed and introduced into a high-pressure reactor and the mixture was heated at 100° C. under a pressure of 12000 atmospheres for 20 hours. The reaction mixture taken out was evaporated and then purified by distillation under reduced pressure to obtain a reaction product which could be identified from the results of the IR and MS analyses shown below to be the desired 1-methyl-4-butoxy-2-azetidinone which was the β-lactam compound of the general formula (I) with $R^1$ and $R^2$ being a methyl group and butyl group, respectively. The yield of the product was 31% of the theoretical value.

IR: 1767 cm$^{-1}$ (lactam C=O);

MS (m/z): 157 (M$^+$) (corresponding to $C_8H_{15}O_2N$).

EXAMPLE 5

A Teflon tube containing a mixture of 0.21 g (3.7 mmoles) of methyl isocyanate and 0.78 g (5.0 mmoles) of 2-ethylhexyl vinyl ether was sealed and introduced into a high-pressure reactor and the mixture was heated at 100° C. under a pressure of 8000 atmospheres for 20 hours. The reaction mixture taken out was purified by the method of dry-column chromatography in a silica gel column with a 2:1 mixture of hexane and ethyl acetate as the eluant to obtain a reaction product which could be identified from the results of the IR and MS analyses shown below to be the desired 1-methyl-4-(2-ethylhexyl)oxy-2-azetidinone which was the β-lactam compound of the general formula (I) with $R^1$ and $R^2$ being a methyl group and 2-ethyl-hexyl group, respectively. The yield of the product was 12% of the theoretical value.

IR: 1769 cm$^{-1}$ (lactam C=O);

MS (m/z): 213 (M$^+$) (corresponding to $C_{12}H_{23}O_2N$).

EXAMPLE 6

A Teflon tube containing a mixture of 0.30 g (3.0 mmoles) of butyl isocyanate and 0.49 g (6.8 mmoles) of ethyl vinyl ether was sealed and introduced into a high-pressure reactor and the mixture was heated at 100° C. under a pressure of 12000 atmospheres for 20 hours. The reaction mixture taken out was evaporated and then purified by distillation under reduced pressure to obtain a reaction product which could be identified from the results of the IR and MS analyses shown below to be the desired 1-butyl-4-ethoxy-2-azetidinone which was the β-lactam compound of the general formula (I) with $R^1$ and $R^2$ being a butyl group and ethyl group, respectively. The yield of the product was 14% of the theoretical value.

IR: 1765 cm$^{-1}$ (lactam C=O);

MS (m/z): 171 (M$^+$) (corresponding to $C_9H_{17}O_2N$).

EXAMPLE 7

A Teflon tube containing a mixture of 0.44 g (3.5 mmoles) of cyclohexyl isocyanate and 0.48 g (6.7 mmoles) of ethyl vinyl ether was sealed and introduced into a high-pressure reactor and the mixture was heated at 100° C. under a pressure of 12000 atmospheres for 20 hours. The reaction mixture taken out was purified by the method of dry-column chromatography in a silica gel column with a 1:1 mixture of hexane and ethyl acetate as the eluant to obtain a reaction product which could be identified from the results of the IR and MS analyses shown below to be the desired 1-cyclohexyl-4-ethoxy-2-azetidinone which was the β-lactam compound of the general formula (I) with $R^1$ and $R^2$ being a cyclohexyl group and ethyl group, respectively. The yield of the product was 4% of the theoretical value.

IR: 1759 cm$^{-1}$ (lactam C=O);

MS (m/z): 197 (M$^+$) (corresponding to $C_{11}H_{19}O_2N$).

EXAMPLE 8

A Teflon tube containing a mixture of 0.40 g (3.0 mmoles) of benzyl isocyanate and 0.44 g (6.1 mmoles) of ethyl vinyl ether was sealed and introduced into a high-pressure reactor and the mixture was heated at 100° C. under a pressure of 8000 atmospheres for 20 hours. The reaction mixture taken out was purified by the method of dry-column chromatography in a silica gel column with a 2:1 mixture of hexane and ethyl acetate as the eluant to obtain a reaction product which could be identified from the results of the IR and MS analyses shown below to be the desired 1-benzyl-4-ethoxy-2-azetidinone which was the β-lactam compound of the general formula (I) with $R^1$ and $R^2$ being a benzyl group and ethyl group, respectively. The yield of the product was 42% of the theoretical value.

IR: 1761 cm$^{-1}$ (lactam C=O);

MS (m/z): 205 (M$^+$) (corresponding to $C_{12}H_{15}O_2N$).

EXAMPLE 9

A Teflon tube containing a mixture of 0.36 g (3.0 mmoles) of phenyl isocyanate, 0.26 g (3.6 mmoles) of ethyl vinyl ether and 2 ml of toluene was sealed and introduced into a high-pressure reactor and the mixture was heated at 100° C. under a pressure of 8000 atmospheres for 20 hours. The reaction mixture taken out was gas-chromatographically analyzed with hexadecane as the internal standard to find that the principal constituent was 1-phenyl-4-ethoxy-2-azetidinone which was the β-lactam compound of the general formula (I) with $R^1$ and $R^2$ being a phenyl group and ethyl group, respectively. The yield of the product was 83% of the theoretical value.

EXAMPLE 10

A Teflon tube containing a mixture of 0.36 g (3.0 mmoles) of phenyl isocyanate and 1.08 g (15 mmoles) of ethyl vinyl ether was sealed and introduced into a high-pressure reactor and the mixture was heated at 70° C. under a pressure of 8000 atmospheres for 20 hours. The reaction mixture taken out was analyzed gas-chromatographically with hexadecane as the internal standard to find that the principal constituent was 1-phenyl-4-ethoxy-2-azetidinone in a yield of 90% of the theoretical value.

EXAMPLE 11

A Teflon tube containing a mixture of 0.16 g (2.8 mmoles) of methyl isocyanate, 0.27 g (3.8 mmoles) of ethyl vinyl ether and 2 ml of toluene was sealed and introduced into a high-pressure reactor and the mixture was heated at 130° C. under a pressure of 8000 atmospheres for 20 hours. The reaction mixture taken out was evaporated and then purified by distillation under reduced pressure to obtain 1-methyl-4-ethoxy-2-azetidinone in a yield of 16% of the theoretical value.

What is claimed is:

1. A method for the preparation of a β-lactam compound represented by the formula

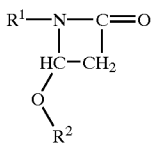

in which $R^1$ is a monovalent hydrocarbon group selected from the group consisting of alkyl groups having 1 to 20 carbon atoms, cycloalkyl groups having 3 to 20 carbon atoms, aryl groups having 6 to 20 carbon atoms and aralkyl groups having 7 to 20 carbon atoms, and $R^2$ is a monovalent hydrocarbon group selected from the group consisting of alkyl groups having 1 to 20 carbon atoms and cycloalkyl groups having 3 to 20 carbon atoms, which comprises the steps of:

(a) mixing an isocyanate compound represented by the formula $R^1NCO$, in which $R^1$ has the same meaning as defined above, and a vinyl ether compound represented by the formula $CH_2=CH-O-R^2$, in which $R^2$ has the same meaning as defined above, to form a reaction mixture; and (b) bringing the reaction mixture under a superatmospheric pressure of at least 2000 atmospheres.

2. The method for the preparation of a β-lactam compound as claimed in claim 1 in which the superatmospheric pressure in step (b) is in the range from 2000 to 12000 atmospheres.

3. The method for the preparation of a β-lactam compound as claimed in claim 1 in which the reaction mixture in step (b) is kept at a temperature in the range from 20 to 130° C.

* * * * *